United States Patent [19]

Anatol et al.

[11] 4,332,959
[45] Jun. 1, 1982

[54] PROCESS FOR MANUFACTURING PHENOXYLACTIC ACIDS, THEIR DERIVATIVES AND PRODUCTS OBTAINED THEREBY

[75] Inventors: Jésus Anatol; Yves Clénet, both of Paris; Georges Bourdiau, Le Bourget, all of France

[73] Assignee: Sucreries du Soissonnais et Compagnie Sucriere, France

[21] Appl. No.: 67,637

[22] Filed: Aug. 17, 1979

[30] Foreign Application Priority Data

Aug. 18, 1978 [FR] France .................. 78 24116

[51] Int. Cl.$^3$ ............................................. C07C 69/76
[52] U.S. Cl. ......................................... 560/60; 560/61; 560/73; 560/106; 560/228; 560/254; 562/470; 562/471; 564/175; 544/170; 546/250; 260/465 F
[58] Field of Search ............... 562/470, 471; 560/60, 560/61, 62, 254, 228, 106, 73; 546/250; 544/170; 260/465 F

[56] References Cited

U.S. PATENT DOCUMENTS

| | | | |
|---|---|---|---|
| 2,719,176 | 9/1955 | Coover | 564/124 |
| 3,113,964 | 12/1963 | Faricas et al. | 564/124 |
| 3,166,588 | 1/1965 | Johnson et al. | 564/170 |
| 3,190,917 | 6/1965 | Johnson et al. | 564/129 |
| 3,277,160 | 10/1966 | Weil | 564/170 |
| 3,641,123 | 2/1972 | Hayman et al. | 564/170 |

FOREIGN PATENT DOCUMENTS 1231685  1/1967  Fed. Rep. of Germany ...... 564/129

OTHER PUBLICATIONS

Krauch, H. et al., "Organic Name Reactions", John Wiley & Sons, N. Y., p. 391, 1964.
Noller, C. R., "Chem. of Organic Cmpds.", W. B. Saunder, p. 276, 1968.

Primary Examiner—Paul J. Killos
Attorney, Agent, or Firm—Karl W. Flocks; Sheridan Neimark

[57] ABSTRACT

The process is for the manufacture of phenoxylactic acids and their derivatives of the general formula:

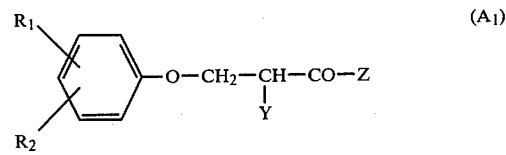

(A$_1$)

(in which R$_1$ and R$_2$, identical or different, can represent hydrogen atoms, methyl residues, methoxy groups or halogens; Y represents an OH or O—CO—R$_3$ group with R$_3$ representing either an aliphatic residue possibly substituted by a halogen, or an aromatic residue possibly substituted on the nucleus by one or several methyl, methoxy, halogen groups or lastly a heterocyclic group; Z represents OH group or an

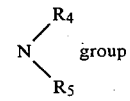

group with R$_4$ representing an alkyl or aryl radical and R$_5$ hydrogen or an alkyl radical, NR$_4$R$_5$ possibly also representing the morpholinyl radical). A cyanhydrin is subjected to a Ritter reaction (reaction with tert. butanol or isobutene in the presence of an acid). The resulting compound is hydrolyzed to obtain the corresponding acid, and if desired, this acid is subjected to conventional reactions for preparing ester-acids, ester-amides or corresponding amides.

5 Claims, No Drawings

PROCESS FOR MANUFACTURING PHENOXYLACTIC ACIDS, THEIR DERIVATIVES AND PRODUCTS OBTAINED THEREBY

The present invention relates to the production of a general class of chemical compounds, namely that of phenoxylactic acids and their derivatives as well as the novel products resulting therefrom.

The compounds according to the invention correspond to the general formula

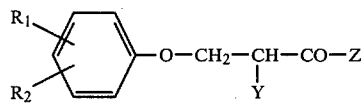
(A)

where
$R_1$ and $R_2$ are identical or different and can represent hydrogen atoms, methyl residues, methoxy groups or halogens;
Y represents an —OH or —O—CO—$R_3$ group with $R_3$ representing either an aliphatic residue possibly substituted by a halogen, or an aromatic residue possibly substituted on the nucleus by one or several methyl, methoxy, halogen groups, or a saturated or unsaturated arylaliphatic residue, or lastly a heterocyclic group;
Z represents the —OH group or an

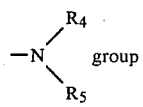

with $R_4$ representing an alkyl or aryl radical and $R_5$ hydrogen or an alkyl radical, —$NR_4R_5$ possibly also representing the morpholinyl radical.

Thus:

In the particular case where Z and Y represent —OH, the compounds of the invention are the phenoxylactic acids themselves of the general formula:

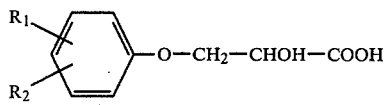
($A_1$)

where $R_1$ and $R_2$ have the above-indicated significance;

In the particular case where Z represents the OH group and Y represents the —O—CO—$R_3$ group, the compounds of the invention are esters in the 2 position of the above acids ($A_1$) corresponding to the general formula:

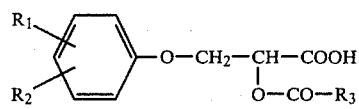
($A_2$)

where $R_1$ and $R_2$ have the above-indicated significance;

In the particular case where Y represents OH and Z represents the

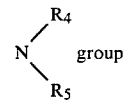

as defined above, the compounds of the invention are the secondary and tertiary amides of the above acids, corresponding to the general formula:

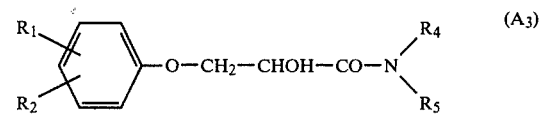
($A_3$)

where $R_1$ and $R_2$ have the above-indicated significance;

and lastly in the particular case where Y represents the —O—CO—$R_3$ group as defined above and Z represents the $NR_4R_5$ group as defined above, the compounds of the invention are the ester-amide derivatives of $A_3$ corresponding to the general formula:

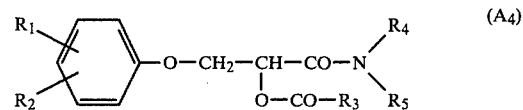
($A_4$)

where $R_1$ and $R_2$ have the previously given significance.

The process according to the invention is essentially characterized by the fact that it consists of subjecting a cyanhydrin of the formula:

$$R_1\text{-}\bigcirc\text{-}O\text{-}CH_2\text{-}CHOH\text{-}CN \quad (A)$$

(where $R_1$ and $R_2$ have the above-given significance) to a RITTER reaction (reaction with tert. butanol or isobutene in the presence of an acid which is generally sulphuric acid) to produce the compound of the formula:

$$R_1\text{-}\bigcirc\text{-}O\text{-}CH_2\text{-}CH(OH)\text{-}CO\text{-}NH\text{-}C(CH_3)_3 \quad (A_{3a})$$

of hydrolysing the latter to obtain the corresponding compound of formula:

$$R_1\text{-}\bigcirc\text{-}O\text{-}CH_2\text{-}CH(OH)\text{-}COOH \quad (A_1)$$

which is then subjected to conventional reactions for preparing the ester-acid of the formula:

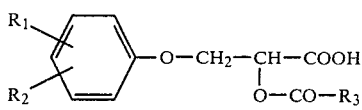

the amide of the formula:

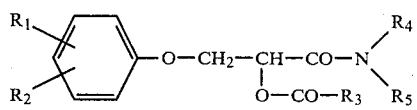

or of the formula:

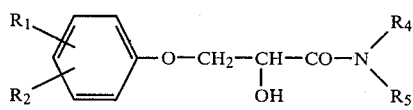

where $R_4$ and $R_5$ have the above-mentioned significance.

The starting cyanhydrin serving for carrying out the process of the invention is obtained from the corresponding phenoxy acetaldehyde using the usual methods for preparing a cyanhydrin from an aldehyde.

These cyanhydrins (3-phenoxy lactonitriles) constitute novel products.

Subjected to the conditions of the RITTER reaction as indicated above, these cyanhydrins lead, with good yields, to the tertiobutylamides ($A_{3a}$) of 3-phenoxy lactic acids of which no representative is mentioned in the literature to the knowledge of Applicants.

The hydrolysis of these tertiobutylamides enables the production of the corresponding 3-phenoxy lactic acids ($A_1$).

With these acids available, the technician skilled in the art then possesses a means enabling the production of the corresponding O-acyl 3-phenoxy lactic acids ($A_2$) of which all the representatives are novel products.

These derivatives treated with chlorinating agents give the corresponding acid chlorides which subjected to the action of amines, can easily be converted into the corresponding ester-amides ($A_4$). In addition, if the latter compounds are subjected to deacylation by selective hydrolysis, the various alpha hydroxyamides of the 3-phenoxy lactic acids are obtained.

These hydroxyamides may in their turn be O-acylated by means of acid chlorides: $R_3$—CO—Cl. This constitutes an interesting route to the $A_4$ derivatives which can thus be obtained:

either from esters in the 2 postion of the phenoxylactic acids;

or from hydroxyamides ($A_3$) obtained for example from an easily available compound $A_4$.

Certain compounds $A_{4a}$ in which $R_4=(CH_3)_3C$ and $R_5=H$ can obviously be produced more directly from hydroxyamides ($A_{3a}$).

The reaction diagram below illustrates the method for preparing the above compounds.

The following examples are given by way of non-limiting illustration.

In these examples, the compounds accompanied by an asterisk (*) are known compounds.

The melting points were measured on a Kofler bank.

Thin layer chromatography (T.L.C.) was carried out on silica gel plates on a plastics support, eluted by the ascending method and developed with a sulphopermanganic mixture. The eluants used were:

| | |
|---|---|
| A: chloroform alone; | C: chloroform/methanol (95/5); |
| B: chloroform/methanol (99/1); | D: chloroform/methanol (90/10). |

REACTION DIAGRAM

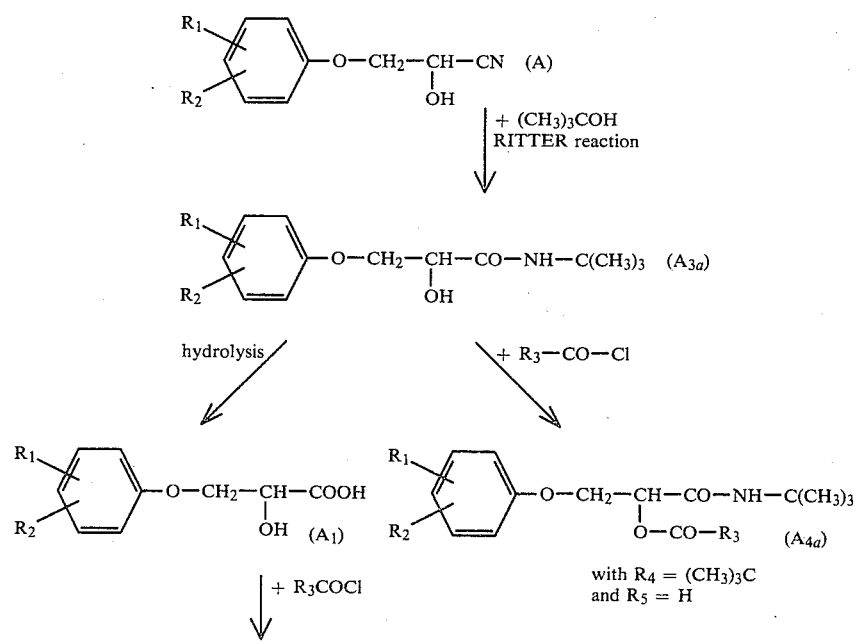

REACTION DIAGRAM

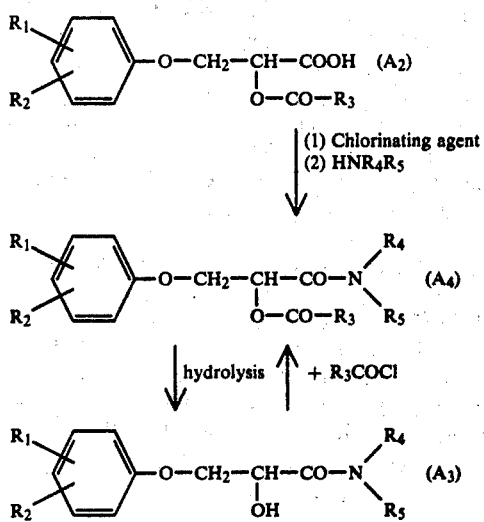

EXAMPLE 1

2-hydroxy 3-phenoxy propanenitrile (A; $R_1=R_2=H$) "Compound No. 1".

In a three neck flask of one liter with a mechanical stirrer, thermometer and bromine funnel, were introduced 136 g (1 mole) of monopotassium phosphate and 408 ml of water. At ambient temperature, 136 g (1 mole) of phenoxy-acetaldehyde was added. A very beautiful precipitate is at once formed and the temperature rises slightly.

With cooling on an ice bath, there was added through the bromine funnel a solution of 65 g (1 mole) of potassium cyanide in 130 ml of water watching so that the temperature of the mixture does not exceed 15° C. The addition takes about 30 minutes. An oil is formed which is emulsified by stirring and which starts to precipitate a little after the end of the addition. The stirring was continued in the ice bath for 30 minutes and then the crystals filtered off, washed with water until neutrality and dried to constant weight. The product obtained melting at about 56° C. was recrystallized in 10 volumes of carbon tetrachloride. In this way a product melting at 59° C. was obtained.

T.L.C.: eluant C a single spot Rf=0.3.

Analysis: $C_9H_9NO_2$. M=163.18. Calculated %: C: 66.24; H: 5.56; N: 8.58. Found %: C: 66.18; H: 5.63; N: 8.73.

Similarly, the cyanhydrins (A) assembled in Table I were obtained:

TABLE I 3-phenoxy lactontriles A:

| Compound No. | $R_1$ | $R_2$ | M.P. °C. | Recrystallisation |
|---|---|---|---|---|
| 1 | H | H | 60 | $CCl_4$ 10 vol. |
| 2 | o-$CH_3$ | H | 60 | $CCl_4$ |
| 3 | p-$CH_3$ | H | 64 | $CCl_4$ |
| 4 | o-$CH_3$ | o'-$CH_3$ | 80 | $CCl_4$ |
| 5 | o-$OCH_3$ | H | 88 | $CCl_4$ 7.5 vol. |
| 6 | p-$OCH_3$ | H | 63 | Trichlorethylene 2 vol. |

TABLE I-continued 3-phenoxy lactontriles A:

| Compound No. | $R_1$ | $R_2$ | M.P. °C. | Recrystallisation |
|---|---|---|---|---|
| 7 | p-Cl | H | 72-5 | $CCl_4$ |

EXAMPLE 2

N-tert.-butyl 2-hydroxy 3-p-tolyloxy propanamide ($A_3$; $R_1$=p-$CH_3$, $R_2=R_5=H$, $R_4=(CH_3)_3C$) Compound No. 10.

Into a 500 ml flask with stirring, refrigeration, thermometer and dropping funnel, to a mixture of 20.4 g (0.115 mole) of 3-p-tolyloxy lactonitrile and 120 ml of tert.-butanol, was added 50 ml of boron trifluoride etherate and then it was kept in a water bath at 50° C. for 2 hours.

It was then run into 500 ml of cold water, the gummy product obtained was separated and it was crystallized in 100 ml of isopropyl ether. After filtration and drying, the product obtained was recrystallized in 12 volumes of ethanol (2 vol.)-isopropyl ether (10 vol.) mixture. M.P.=141°-2° C.

T.L.C.: elution with a single spot $R_f$=0.4.

Analysis: $C_{14}H_{21}NO_3$. M=251.34. Calculated: C: 66.91; H: 8.42; N: 5.57. Found: C: 66.66; H: 8.54; N: 5.55. 66.61; 8.40.

I.R. spectrum (1% KBr tablet): bands at 3375 (CO—NH—), 3200 (OH), 1640-60 cm$^{-1}$ (CO—NH).

The 2-N-tert.-butyl hydroxy 3-aryloxy propanamides ($A_{3a}$) assembled in the following table were obtained similarly.

TABLE II

N-tert.-butyl 2-hydroxy 3-aryloxy propanamides ($A_{3a}$)

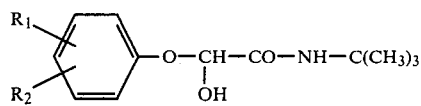

| Compound No. | $R_1$ | $R_2$ | M.P. °C. | Recrystal- lisation | T.L.C. eluant | Rf |
|---|---|---|---|---|---|---|
| 8 | H | H | 123 | CCl$_4$ 3 vol. | B | 0.36 |
| 9 | o-CH$_3$ | H | 80 | hexane 10 vol. | B | 0.45 |
| 10 | p-CH$_3$ | H | 141 | EtOH 2 vol. + isopropyl ether 10 vol. | A | 0.40 |
| 11 | o-CH$_3$ | o'-CH$_3$ | 130 | AcOEt 4 vol. | A | 0.38 |
| 12 | o-OCH$_3$ | H | 96 | Isopropyl ether 4 vol. | C | 0.27 |
| 13 | p-OCH$_3$ | H | 100-4 | Isopropyl ether 5 vol. | C | 0.30 |
| 14 | p-Cl | H | 130 | MeOH 1 vol. + isopropyl ether 4.5 vol. | D | 0.75 |

EXAMPLE 3

2-hydroxy 3-p-chlorophenoxy propanoic acid ($A_1$; $R_1$=p-Cl, $R_2$=H) Compound No. 21.

A mixture of 5.43 g (0.02 mole) of N-tert.-butyl 2-hydroxy 3-p-chlorophenoxy propanamide in 16.3 ml of water, 16.3 ml of concentrated hydrochloric acid (d=1.18) and 5.4 ml of acetic acid was brought to reflux for 3 h 45 until the solution became clear. On cooling, the product crystallized. It was filtered, washed with water and dried. It was recrystallizable in water (40 vol.). Crystals in flakes M.P.=138° C.

T.L.C.: eluant C. Rf=0.48.

Analysis: C$_9$H$_9$ClO$_4$. M=216.62. Calculated: C: 49.90; H: 4.19. Found: C: 50.02; H: 4.08.

I.R. spectrum (1% KBr tablet): bands at 3350 (OH) and 1715 cm$^{-1}$ (COOH).

The 3-aryloxy lactic acids ($A_1$) obtained similarly are assembled in Table III.

TABLE III 3-aryloxy lactic acids ($A_1$):

| Compound No. | $R_1$ | $R_2$ | M.P. °C. | Recrystal- lisation | T.L.C. eluant | Rf |
|---|---|---|---|---|---|---|
| 15* | H | H | 160 | water 4 vol. | D | 0.58 |
| 16* | o-CH$_3$ | H | 145 | water 10 vol. | C | 0.53 |
| 17 | p-CH$_3$ | H | 153 | water 10 vol. | D | 0.26 |
| 18 | o-CH$_3$ | o'-CH$_3$ | 137 | water 10 vol. | D | 0.75 |
| 19* | o-OCH$_3$ | H | ~90 | poorly recrystal- lizing oil | D | 0.34 |
| 20 | p-OCH$_3$ | H | 160 | EtOH 6 vol. | D | 0.44 |
| 21 | p-Cl | H | 137 | water 40 vol. | C | 0.42 |

EXAMPLE 4

2-acetoxy 3-(p-chlorophenoxy) propanoic acid.

($A_2$; $R_1$=p-Cl, $R_2$=H, $R_3$=CH$_3$) Compound No. 22

To 38.97 g (0.18 mole) of 2-hydroxy 3-p-chlorophenoxy propanoic acid placed in a 250 ml flask surmounted by a refrigerating column provided with a calcium chloride trap, was added 58.5 ml of acetyl chloride and it was kept in a bath at 45° C. for 4 h. It was concentrated on a rotary evaporator, the residue was taken up again with toluene which was driven off to remove the excess acetyl chloride. The residue was dissolved in 180 ml of a 10% aqueous sodium bicarbonate solution. The solution obtained was treated with animal black at ambient temperature for 15 minutes and then filtered on paper. The colorless solution obtained was acidified to pH=1 with 2 N hydrochloric acid.

The precipitate obtained was filtered, washed with water and dried.

M.P.=51.5°-52.5° (capillary).

It was a monohydrate which, dried in a vacuum dessicator, was converted into an oil.

T.L.C.: eluant C. Rf=0.31.

Analysis: C$_{11}$H$_{11}$ClO$_5$: 1 H$_2$O. M=276.67. Calculated %: C: 47.75; H: 4.73. Found %: C: 47.74; H: 4.52; C: 47.95; H: 4.51

I.R. spectrum (1% KBr tablet): band at 1750 cm$^{-1}$ (COOH).

EXAMPLE 5

In the same way, there was obtained:

2-acetoxy 3-phenoxy propanoic acid ($A_2$; $R_1$=$R_2$=H, $R_3$=CH$_3$) Compound No. 23 which was also purified through its sodium salt obtained by means of sodium carbonate. M.P.=109° C.

T.L.C.: eluant D. Rf=0.71.

Analysis: C$_{11}$H$_{12}$O$_5$. M=224.21. Calculated %: C: 58.93; H: 5.39. Found %: C: 59.07; H: 5.42; C: 59.04; H: 5.46.

I.R. spectrum (1% KBr tablet): bands at 1760 and 1710 cm$^{-1}$ (CO acid and CO ester).

EXAMPLE 6

(a) 3-phenoxy 2-acetoxy propionyl chloride

To 22.42 g (0.1 mole) of 2-acetoxy 3-phenoxy propanoic acid, was added 24 g of thionyl chloride and the mixture was heated under reflux for 2 hours. The excess of thionyl chloride was driven off on a rotary evaporator and the residue was distilled under nitrogen. B.P.$_{.14}$=163°-8° C.

(b) N-morpholino 2-acetoxy 3-phenoxy propanamide ($A_4$; $R_1$=$R_2$=H, $R_3$=CH$_3$, NR$_4$R$_5$-morpholinyl) Compound No. 45.

To 1.73 ml (0.02 mole) of morpholine in solution in 25 ml of isopropyl ether, were added 2.42 g (0.01 mole) of 2-acetoxy 3-phenoxy propionyl chloride in solution in 15 ml of isopropyl ether. The morpholine hydrochloride precipitated at once. After 4 hours of stirring at ambient temperature, the precipitate was filtered off and washed with a little isopropyl ether. The filtrate was dried. The residue obtained was dissolved in chloroform, washed with water and concentrated to dryness. The residue was recrystallized in a mixture of 1 volume of carbon tetrachloride and 9 volumes of isopropyl ether. M.P.=89° C.

T.L.C.: eluant B. Rf=0.55.

Analysis: C$_{15}$H$_{19}$NO$_5$. M=293.33. Calculated %: C: 61.42; H: 6.53; N:4.78. Found %: C: 61.33; H: 6.74; N: 4.87.

I.R. spectrum (1% KBr tablet): bands at 1745 (CO ester) and 1655 cm$^{-1}$ (CO amide).

EXAMPLE 7

N-isopropyl 2-hydroxy 3-(p-chlorophenoxy) propanamide ($A_3$: $R_1$=p-Cl, $R_2$=$R_5$=H, $R_4$=$(CH_3)_2CH$) Compound No. 24.

To 3 g (0.01 mole) of N-isopropyl 2-acetoxy 3-(p-chlorophenoxy) propanamide, was added 9 ml of alcohol and 4 ml of a 10% soda solution with magnetic stirring. A yellow solution was obtained which was heated on the water bath for a half hour. On cooling, the product recrystallized. It was filtered, washed with water, dried and finally recrystallized in 5 volumes of ethyl acetate. M.P.=117° C.

T.L.C.: eluant D. Rf=0.50.

Analysis: $C_{12}H_{16}ClNO_3$. M=252,72. Calculated %: C: 55.93; H: 6.26; N: 5.43. Found %: C: 55.76; H: 6.18; N: 5.40.

I.R. spectrum (1% KBr tablet): bands at 3370 (OH), 3320 (NH), 1640-60 cm$^{-1}$ (CONH).

EXAMPLE 8

N-isopropyl 2-hydroxy 3-phenoxy propanamide ($A_3$; $R_1$=$R_2$=$R_5$=H, $R_4$=$(CH_3)_2CH$) Compound No. 25.

This product was obtained as in Example 7 from 2.65 g of N-isopropyl 2-acetoxy 3-phenoxy propanamide. M.P.=68°-70° C. (isopropyl ether 4 volumes).

T.L.C.: eluant B. Rf=0.33.

Analysis: $C_{12}H_{17}NO_3$ M=223.27 Calculated %: C: 64.55 H: 7.67 N: 6.27 Found %: 64.29 7.79 6.22 64.36 7.85

I.R. spectrum (1% KBr tablet): bands at 3380 (OH), 3320 (NH), 1630 cm$^{-1}$ (CONH).

EXAMPLE 9

N-isopropyl 2-(3,4,5-trimethoxy benzoyloxy) 3-(p-chlorophenoxy) propanamide ($A_4$; $R_1$=p-Cl, $R_2$=$R_5$=H, $R_3$=3,4,5 $(MeO)_3C_6H_2$, $R_4$=$(CH_3)_2CH$) Compound No. 110.

To 5.15 g (0.02 mole) of N-isopropyl 2-hydroxy 3-(p-chlorophenoxy) propanamide, 50 ml of toluene and 3.35 ml (0.024 mole) of triethylamine, was added 5.07 g (0.022 mole) of 3,4,5-trimethoxy benzoyl chloride and the mixture was brought to reflux with stirring for 4 hours. After cooling, the mixture was taken up with 70 ml of chloroform, washed successively with water, with a 2 N solution of soda and finally with water. Dried over sodium sulphate. The residue obtained, after evaporation of the solvent, was recrystallized in 8 volumes of alcohol. M.P.=151° C.

T.L.C.: eluant C. Rf=0.6

Analysis: $C_{22}H_{26}ClNO_7$. M=451.91 Calculated %: C: 58.47; H: 5.80; N: 3.10. Found %: C: 58.47; H: 5.68; N: 3.11.

I.R. spectrum (1% KBr tablet): bands at 3260 (NH), 1730 (CO ester) and 1655 cm$^{-1}$ (CO amide).

EXAMPLE 10

N-tert.-butyl 2-(trans-cinnamoyloxy) 3-(2,6-dimethyl phenoxy) propanamide ($A_4$; $R_1$=o-$CH_3$, $R_2$=o'-$CH_3$, $R_3$=$C_6H_5$—CH=CH, $R_4$=$(CH_3)_3C$, $R_5$=H) Compound No. 58.

To 5.3 g (0.02 mole) of N-tert.-butyl 2-hydroxy 3-(2,6- dimethyl phenoxy) propanamide, 50 ml of toluene and 3,35 ml of triethylamine, was added 3.66 g (0.022 mole) of trans-cinnamoyl chloride and the mixture was heated on an oil bath at 140° C. for 4 hours. After cooling, taking up again in chloroform and washings as in Example 9, the product obtained after the evaporation was recrystallized in 10 volumes of isopropyl ether. M.P.=108° C.

T.L.C.: eluant A Rf=0.6.

Analysis: $C_{24}H_{29}NO_4$. M=395.5. Calculated %: C: 72.88; H: 7.39; N: 3.54. Found %: C: 72.53; H: 7.42; N: 3.57.

I.R. spectrum (1% KBr tablet): bands at 3260 (NH), 1720 (CO ester), 1670 (CO amide) and 1640 cm$^{-1}$ (double bond).

The amides of the O-acylated derivatives of the phenoxy lactic acids (Compounds $A_4$) which are obtained in accordance with the cases in Example 6 (from esters at the 2 position of the phenoxy lactic acids), 9 (from hydroxy amides $A_3$) or 10 (from Ritter hydroxy amides $A_{3a}$) are assembled in Table IV.

TABLE IV 2-acyloxy 3-phenoxy propanamides:

$$R_1\text{-}C_6H_3(R_2)\text{-}O\text{-}CH_2\text{-}CH(O\text{-}CO\text{-}R_3)\text{-}CO\text{-}N(R_4)(R_5)$$

| Compound No. | $R_1$ | $R_2$ | $R_3$ | $R_4$ | $R_5$ | M.P. °C. | Recrystallisation | T.L.C. Eluant | Rf |
|---|---|---|---|---|---|---|---|---|---|
| 26 | H | H | $CH_3$ | $C(CH_3)_3$ | H | 53 | Cyclohexane 5 vol. | B | 0.60 |
| 27 | H | H | $C_6H_5$ | $C(CH_3)_3$ | H | 141 | EtOH 4.5 vol. | B | 0.71 |
| 28 | H | H | p-$CH_3$—$C_6H_4$ | $C(CH_3)_3$ | H | 88 | Hexane 10 vol. | B | 0.78 |
| 29 | H | H | p-Cl—$C_6H_4$ | $C(CH_3)_3$ | H | 123 | Ether iso 15 vol. | B | 0.80 |
| 30 | H | H | $C_6H_5$—$CH_2$—$CH_2$ | $C(CH_3)_3$ | H | 57 | Petroleum ether 3 vol. + cyclohexane 1.5 vol. | B | 0.80 |
| 31 | H | H | 3-pyridyl | $C(CH_3)_3$ | H | 112 | Ether iso 5 vol. + $CCl_4$ 2.5 vol. | C | 0.84 |
| 32 | H | H | $CH_3$ | $CH(CH_3)_2$ | H | 109 | $CCl_4$ 5 vol. + ether iso 14 vol. | B | 0.57 |
| 33 | H | H | $CH_3(CH_2)_{14}$ | $CH(CH_3)_2$ | H | 73 | EtOH 14 vol. | B | 0.66 |
| 34 | H | H | $C_6H_5$ | $CH(CH_3)_2$ | H | 139 | EtOH 5.5 vol. | B | 0.56 |
| 35 | H | H | p-$CH_3$—$C_6H_4$ | $CH(CH_3)_2$ | H | 133 | EtOH 5.5 vol. | B | 0.56 |
| 36 | H | H | p-$CH_3O$—$C_6H_4$ | $CH(CH_3)_2$ | H | 132 | EtOH 2,75 vol. + ether iso 2.75 vol. | B | 0.57 |
| 37 | H | H | p-Cl—$C_6H_4$ | $CH(CH_3)_2$ | H | 151 | MeOH 14 vol. | B | 0.67 |
| 38 | H | H | p-$NO_2$—$C_6H_4$ | $CH(CH_3)_2$ | H | 175 | AcOEt 11.5 vol. | not revealed | |
| 39 | H | H | p-$NH_2$—$C_6H_4$ | $CH(CH_3)_2$ | H | 173 | EtOH 29 vol. | B | 0.36 |
| 40 | H | H | 3,4,5$(CH_3O)_3C_6H_2$ | $CH(CH_3)_2$ | H | 145 | EtOH 5 vol. | B | 0.47 |

TABLE IV-continued 2-acyloxy 3-phenoxy propanamides:

$$\begin{array}{c}R_1\\R_2\end{array}\!\!-\!\!\text{C}_6\text{H}_3\!-\!\text{O}-\text{CH}_2-\underset{\underset{\text{O}-\text{CO}-R_3}{|}}{\text{CH}}-\text{CO}-\text{N}\begin{array}{c}R_4\\R_5\end{array}$$

| Compound No. | $R_1$ | $R_2$ | $R_3$ | $R_4$ | $R_5$ | M.P. °C. | Recrystallisation | T.L.C. Eluant | Rf |
|---|---|---|---|---|---|---|---|---|---|
| 41 | H | H | $C_6H_5$—CH=CH | $CH(CH_3)_2$ | H | 134 | MeOH 4 vol. | B | 0.66 |
| 42 | H | H | $C_6H_5$—$CH_2$—$CH_2$ | $CH(CH_3)_2$ | H | 73 | Ether iso 5 vol. | B | 0.58 |
| 43 | H | H | 3-pyridyl | $CH(CH_3)_2$ | H | 143 | AcOEt 7 vol. | B | 0.21 |
| 44 | H | H | $CH_3$ | $C_6H_5$ | H | 81 | Ether iso 10 vol. | B | 0.67 |
| 45 | H | H | $CH_3$ | $(CH_2)_2$—O—$(CH_2)_2$ | | 89 | $CCl_4$ 1 vol. + ether iso 9 vol. | B | 0.48 |
| 46 | o-$CH_3$ | H | 3,4,5($CH_3O)_3C_6H_2$ | $C(CH_3)_3$ | H | 129 | ether iso 20 vol. | C | 0.95 |
| 47 | o-$CH_3$ | H | $C_6H_5$—CH=CH | $C(CH_3)_3$ | H | 86 | iso-PrOH 4 vol. | B | 0.71 |
| 48 | p-$CH_3$ | H | $CH_3$ | $C(CH_3)_3$ | H | 76 | ether iso 5 vol. | A | 0.51 |
| 49 | p-$CH_3$ | H | p-$CH_3$—$C_6H_4$ | $C(CH_3)_3$ | H | 106 | ether iso 10 vol. | A | 0.65 |
| 50 | p-$CH_3$ | H | p-Cl—$C_6H_4$ | $C(CH_3)_3$ | H | 142 | EtOH 6 vol. | A | 0.62 |
| 51 | p-$CH_3$ | H | p-$NO_2$—$C_6H_4$ | $C(CH_3)_3$ | H | 158 | EtOH 18 vol. | A | 0.54 |
| 52 | p-$CH_3$ | H | p-$NH_2$—$C_6H_4$ | $C(CH_3)_3$ | H | 122 | EtOH 2 vol. + hexane 15 vol. | C | 0.42 |
| 53 | p-$CH_3$ | H | 3,4,5($CH_3O)_3C_6H_2$ | $C(CH_3)_3$ | H | 97 | ether iso 11.5 vol. | A | 0.43 |
| 54 | p-$CH_3$ | H | $C_6H_5$—CH=CH | $C(CH_3)_3$ | H | 125 | EtOH 5 vol. | A | 0.59 |
| 55 | p-$CH_3$ | H | 3-pyridyl | $C(CH_3)_3$ | H | 132 | EtOH 1.5 vol. + ether iso 24.5 vol. | A | 0.39 |
| 56 | o-$CH_3$ | o'-$CH_3$ | $CH_3(CH_2)_{14}$ | $C(CH_3)_3$ | H | 80 | Iso-PrOH | A | 0.61 |
| 57 | o-$CH_3$ | o'-$CH_3$ | 3,4,5($CH_3O)_3C_6H_2$ | $C(CH_3)_3$ | H | 112 | iso-PrOH 5 vol. | A | 0.46 |
| 58 | o-$CH_3$ | o'-$CH_3$ | $C_6H_5$—CH=CH | $C(CH_3)_3$ | H | 108 | ether iso 10 vol. | A | 0.60 |
| 59 | o-$CH_3$ | o'-$CH_3$ | 3-pyridyl | $C(CH_3)_3$ | H | 125 | ether iso 15 vol. | A | 0.35 |
| 60 | o-$CH_3O$ | H | $CH_3$ | $C(CH_3)_3$ | H | 88 | ether iso 6 vol. | B | 0.53 |
| 61 | o-$CH_3O$ | H | Cl—$CH_2$ | $C(CH_3)_3$ | H | 103 | ether iso 11.5 vol. | B | 0.60 |
| 62 | o-$CH_3O$ | H | $CH_3$—$(CH_2)_{14}$ | $C(CH_3)_3$ | H | 66 | hexane 5 vol. | B | 0.67 |
| 63 | o-$CH_3O$ | H | $C_6H_5$ | $C(CH_3)_3$ | H | 135 | MeOH 4 vol. | C | 0.44 |
| 64 | o-$CH_3O$ | H | p-$CH_3$—$C_6H_4$ | $C(CH_3)_3$ | H | 137 | EtOH 6 vol. | B | 0.64 |
| 65 | o-$CH_3O$ | H | p-$CH_3O$—$C_6H_4$ | $C(CH_3)_3$ | H | 136 | iso-PrOH 5 vol. | B | 0.53 |
| 66 | o-$CH_3O$ | H | p-Cl—$C_6H_4$ | $C(CH_3)_3$ | H | 154 | EtOH 7 vol. | B | 0.60 |
| 67 | o-$CH_3O$ | H | p-$NO_2$—$C_6H_4$ | $C(CH_3)_3$ | H | 144 | EtOH 7 vol. | B | 0.79 |
| 68 | o-$CH_3O$ | H | p-$NH_2$—$C_6H_4$ | $C(CH_3)_3$ | H | 145 | EtOH 7 vol. | B | 0.41 |
| 69 | o-$CH_3O$ | H | 3,4,5($CH_3O)_3C_6H_2$ | $C(CH_3)_3$ | H | 113 | ether iso 20 vol. | B | 0.79 |
| 70 | o-$CH_3O$ | H | $C_6H_5$—CH=CH | $C(CH_3)_3$ | H | 152 | AcOEt 7 vol. | B | 0.77 |
| 71 | o-$CH_3O$ | H | $C_6H_5$—$CH_2$—$CH_2$ | $C(CH_3)_3$ | H | 75 | hexane 11.5 vol. | B | 0.53 |
| 72 | o-$CH_3O$ | H | 3-pyridyl | $C(CH_3)_3$ | H | 98 | ether iso 9 vol. | C | 0.73 |
| 73 | o-$CH_3O$ | H | $CH_3$ | $CH(CH_3)_2$ | H | 87 | digestion in hexane | C | 0.78 |
| 74 | p-$CH_3O$ | H | $CH_3$ | $C(CH_3)_3$ | H | 75 | ether iso 3 vol. + cyclohexane 1 vol. | C | 0.45 |
| 75 | p-$CH_3O$ | H | Cl—$CH_2$ | $C(CH_3)_3$ | H | 93 | ether iso 6 vol. | C | 0.45 |
| 76 | p-$CH_3O$ | H | $CH_3$—$(CH_2)_{14}$ | $C(CH_3)_3$ | H | 55 | MeOH 3 vol. | C | 0.81 |
| 77 | p-$CH_3O$ | H | $C_6H_5$ | $C(CH_3)_3$ | H | 124 | EtOH 1 vol. + ether iso 5 vol. | C | 0.45 |
| 78 | p-$CH_3O$ | H | p-$CH_3$—$C_6H_4$ | $C(CH_3)_3$ | H | 90 | iso-PrOH 3 vol. | C | 0.45 |
| 79 | p-$CH_3O$ | H | p-$CH_3O$—$C_6H_4$ | $C(CH_3)_3$ | H | 128 | MeOH 5 vol. | B | 0.60 |
| 80 | p-$CH_3O$ | H | p-Cl—$C_6H_4$ | $C(CH_3)_3$ | H | 110 | MeOH 7 vol. | C | 0.50 |
| 81 | p-$CH_3O$ | H | p-$NO_2$—$C_6H_4$ | $C(CH_3)_3$ | H | 110 | EtOH 10 vol. | C | 0.55 |
| 82 | p-$CH_3O$ | H | p-$NH_2$—$C_6H_4$ | $C(CH_3)_3$ | H | 151 | MeOH 7 vol. | C | 0.36 |
| 83 | p-$CH_3O$ | H | 3,4,5($CH_3O)_3C_6H_2$ | $C(CH_3)_3$ | H | 131 | MeOH 7 vol. | C | 0.43 |
| 84 | p-$CH_3O$ | H | $C_6H_5$—CH=CH | $C(CH_3)_3$ | H | 130 | MeOH 7 vol. | C | 0.43 |
| 85 | p-$CH_3O$ | H | $C_6H_5$—$CH_2$—$CH_2$ | $C(CH_3)_3$ | H | 95 | MeOH 4 vol. | C | 0.53 |
| 86 | p-$CH_3O$ | H | 3-pyridyl | $C(CH_3)_3$ | H | 116 | EtOH 1 vol. + ether iso 5 vol. | C | 0.29 |
| 87 | p-Cl | H | $CH_3$ | $C(CH_3)_3$ | H | 104 | cyclohexane 5 vol. | D | 0.95 |
| 88 | p-Cl | H | Cl—$CH_2$ | $C(CH_3)_3$ | H | 96 | iso-PrOH 3 vol. | C | 0.59 |
| 89 | p-Cl | H | $CH_3$—$(CH_2)_{14}$ | $C(CH_3)_3$ | H | 60 | ether iso 5 vol. | C | 0.73 |
| 90 | p-Cl | H | $C_6H_5$ | $C(CH_3)_3$ | H | 152 | ether iso | B | 0.69 |
| 91 | p-Cl | H | p-$CH_3$—$C_6H_4$ | $C(CH_3)_3$ | H | 105 | iso-PrOH 4 vol. | D | 0.96 |
| 92 | p-Cl | H | p-$CH_3O$—$C_6H_4$ | $C(CH_3)_3$ | H | 139 | EtOH 9.5 vol. | B | 0.80 |
| 93 | p-Cl | H | p-Cl—$C_6H_4$ | $C(CH_3)_3$ | H | 152 | EtOH 12 vol. | C | 0.66 |
| 94 | p-Cl | H | p-$NO_2$—$C_6H_4$ | $C(CH_3)_3$ | H | 157 | EtOH 12 vol. | B | 0.50 |
| 95 | p-Cl' | H | p-$NH_2$—$C_6H_4$ | $C(CH_3)_3$ | H | 158 | EtOH 10 vol. | B | 0.56 |
| 96 | p-Cl | H | 3,4,5($CH_3O)_3C_6H_2$ | $C(CH_3)_3$ | H | 118 | ether iso 8 vol. | C | 0.86 |
| 97 | p-Cl | H | $C_6H_5$—CH=CH | $C(CH_3)_3$ | H | 128 | cyclohexane 9 vol. | D | 0.97 |
| 98 | p-Cl | H | $C_6H_5$—CH—$CH_2$ | $C(CH_3)_3$ | H | 62 | hexane 5 vol. | B | 0.63 |
| 99 | p-Cl | H | 3-pyridyl | $C(CH_3)_3$ | H | 143 | EtOH 2 vol. + ether iso 2 vol. | C | 0.39 |
| 100 | p-Cl | H | $CH_3$ | $CH(CH_3)_2$ | H | 108 | EtOH 7.5 vol. + water 7.5 vol. | C | 0.59 |
| 101 | p-Cl | H | Cl—$CH_2$ | $CH(CH_3)_2$ | H | 88 | ether iso 6 vol. | C | 0.61 |
| 102 | p-Cl | H | $(CH_3)_2$CH—$CH_2$ | $CH(CH_3)_2$ | H | 76 | cyclohexane 5 vol. | C | 0.54 |
| 103 | p-Cl | H | $CH_3$—$(CH_2)_{14}$ | $CH(CH_3)_2$ | H | 74 | EtOH 5 vol. | C | 0.68 |
| 104 | p-Cl | H | $C_6H_5$ | $CH(CH_3)_2$ | H | 144 | EtOH 10 vol. | C | 0.63 |
| 105 | p-Cl | H | p-$CH_3$—$C_6H_4$ | $CH(CH_3)_2$ | H | 138 | EtOH 5 vol. | C | 0.76 |

TABLE IV-continued 2-acyloxy 3-phenoxy propanamides:

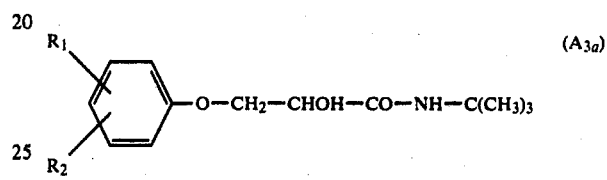

| Compound No. | R₁ | R₂ | R₃ | R₄ | R₅ | M.P. °C. | Recrystallisation | T.L.C. Eluant | Rf |
|---|---|---|---|---|---|---|---|---|---|
| 106 | p-Cl | H | p-CH₃O—C₆H₄ | CH(CH₃)₂ | H | 136 | EtOH 6 vol. | C | 0.53 |
| 107 | p-Cl | H | p-Cl—C₆H₄ | CH(CH₃)₂ | H | 176 | AcOEt 12 vol. | C | 0.70 |
| 108 | p-Cl | H | p-NO₂—C₆H₄ | CH(CH₃)₂ | H | 182 | AcOH 7 vol. | C | 0.46 |
| 109 | p-Cl | H | p-NH₂—C₆H₄ | CH(CH₃)₂ | H | 150 | EtOH 7 vol. | C | 0.38 |
| 110 | p-Cl | H | 3,4,5(CH₃O)₃C₆H₂ | CH(CH₃)₂ | H | 151 | EtOH 8 vol. | C | 0.62 |
| 111 | p-Cl | H | C₆H₅—CH=CH | CH(CH₃)₂ | H | 136 | EtOH 5 vol. | C | 0.70 |
| 112 | p-Cl | H | C₆H₅—CH₂—CH₂ | CH(CH₃)₂ | H | 111 | EtOH 8 vol. | C | 0.66 |
| 113 | p-Cl | H | 3-pyridyl | CH(CH₃)₂ | H | 160 | EtOH 6 vol. | C | 0.33 |
| 114 | p-Cl | H | CH₃ | (CH₂)₂—O—(CH₂)₂ | | 77 | cyclohexane 9 vol. | C | 0.45 |
| 115 | p-Cl | H | CH₃ | C₆H₅ | H | 102 | ether iso 7 vol. | C | 0.55 |

It is self-evident that the present invention has only been described in a purely explanatory and nonlimiting manner and that any useful modification could be introduced therein without departing from its scope as defined by the appended claims.

We claim:

1. Process for the manufacture of phenoxylactic acids and their derivatives of the general formula:

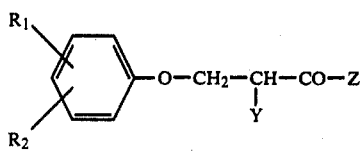

(A₁)

(in which R₁ and R₂, identical or different, can represent hydrogen atoms, methyl residues, methoxy groups or halogens; Y represents an OH or O—CO-R₃ group with R₃ representing either an aliphatic residue optionally substituted with a halogen, or an aromatic residue optionally substituted on the nucleus with one or several methyl, methoxy, halogen groups or a pyridyl group; Z represents OH group or an $$\begin{array}{c} R_4 \\ N \\ R_5 \end{array} \text{group}$$

with R₄ representing an alkyl or aryl radical and R₅ hydrogen or an alkyl radical, or NR₄R₅ represents the morpholinyl radical), which process consists of subjecting a cyanhydrin of the formula:

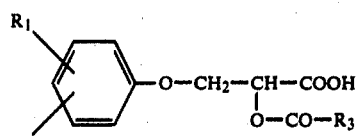

(A)

(where R₁ and R₂ have the above-mentioned significance) to a reaction with tert. butanol or isobutene in the presence of an acid to obtain the compound of the formula:

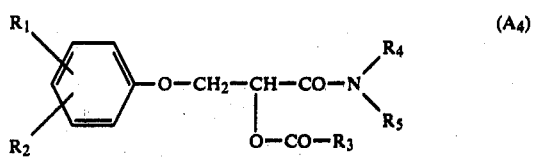

(A₃ₐ)

and of hydrolysing the latter to obtain the corresponding acid of formula (A₁) as defined above, in which Z and Y represent —OH, then, optionally, subjecting this acid to conventional reactions for preparing ester-acids, ester-amides or corresponding amides respectively of the formula:

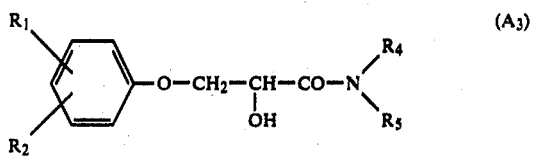

(A₂)

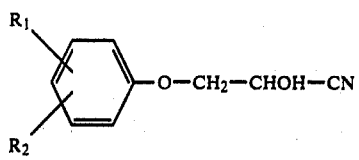

(A₄)

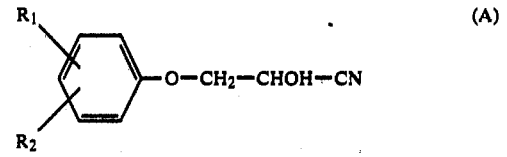

(A₃)

(where R₁ and R₂, R₃, R₄ and R₅ have the above significance).

2. Process according to claim 6 wherein said compound of the formula

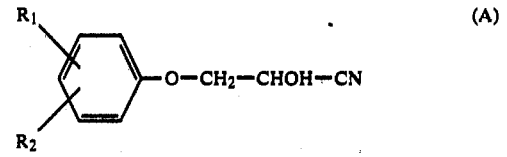

(A)

is obtained by reacting a corresponding phenoxy acetaldehyde

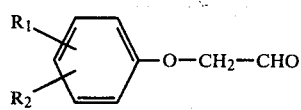

(wherein $R_1$ and $R_2$, identical or different, can represent hydrogen atoms, methyl residues, methoxy groups or halogens) with an aqueous alkaline cyanide solution optionally in the presence of dihydrogen potassium phosphate.

3. Process according to claim 1, in which the compound (A) is selected from among:
2-hydroxy 3-phenoxy propanenitrile
2-hydroxy 3-(o-tolyloxy) propanenitrile
2-hydroxy 3-(p-tolyloxy) propanenitrile
2-hydroxy 3-(dimethyl-2,6 phenoxy) propanenitrile
2-hydroxy 3-(o-methoxy phenoxy) propanenitrile
2-hydroxy 3-(p-methoxy phenoxy) propanenitrile
2-hydroxy 3-(p-chloro phenoxy) propanenitrile.

4. 3-aryloxy lactic acids and 3-aryloxy O-acyl lactic acids, prepared by the process according to claim 1 and corresponding to the formula ($A_1$) as defined and in which Z and Y represent OH.

5. 2-hydroxy and 2-acyloxy 3-aryloxy propanamides as obtained by the process according to claim 1 and corresponding to one of the formulae $A_3$ or $A_4$ as defined therein.

* * * * *